(12) United States Patent
Thornton

(10) Patent No.: US 7,247,162 B1
(45) Date of Patent: Jul. 24, 2007

(54) DIRECT ACCESS ATHERECTOMY DEVICES

(75) Inventor: Peter Thornton, Los Altos, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 365 days.

(21) Appl. No.: 10/164,353

(22) Filed: Jun. 4, 2002

Related U.S. Application Data

(63) Continuation-in-part of application No. 10/046,890, filed on Jan. 14, 2002, now abandoned.

(51) Int. Cl.
*A61M 29/00* (2006.01)

(52) U.S. Cl. ...................... 606/200; 600/104
(58) Field of Classification Search ............... 606/200, 606/127, 159, 170, 194; 600/104
See application file for complete search history.

(56) References Cited

U.S. PATENT DOCUMENTS

| | | | |
|---|---|---|---|
| 4,557,255 A * | 12/1985 | Goodman .................. 600/104 |
| 4,794,931 A | 1/1989 | Yock |
| 4,886,061 A | 12/1989 | Fischell et al. |
| 5,100,425 A | 3/1992 | Fischell et al. |
| 5,402,790 A | 4/1995 | Jang et al. |
| 5,417,697 A * | 5/1995 | Wilk et al. .................. 606/113 |
| 5,582,178 A | 12/1996 | Yock |
| 5,662,671 A | 9/1997 | Barbut et al. |
| 5,759,187 A * | 6/1998 | Nakao et al. ............... 606/114 |
| 5,769,816 A | 6/1998 | Barbut et al. |
| 5,846,260 A | 12/1998 | Maahs |
| 6,001,118 A * | 12/1999 | Daniel et al. ............... 606/200 |
| 6,007,557 A | 12/1999 | Ambrisco et al. |

* cited by examiner

*Primary Examiner*—Michael J. Hayes
*Assistant Examiner*—Victor X. Nguyen
(74) *Attorney, Agent, or Firm*—David L. Hauser

(57) ABSTRACT

An atherectomy device comprising cannula systems having lumens adapted for insertion of a blood filter and an atherectomy catheter useful for performing atherectomy directly on a patient's cardiovascular tissue. Other embodiments include a lumen for arterial perfusion useful in providing oxygenated blood to the aorta during cardiopulmonary bypass. The distal end of the atherectomy catheter includes an assembly that comprises a pincer, a loop with or without a mesh, laser, hydraulics, or other suitable mechanism adapted for removing atheroma from a cardiac or vascular tissue. Methods of using the systems for vascular atherectomy are also disclosed herein.

7 Claims, 4 Drawing Sheets

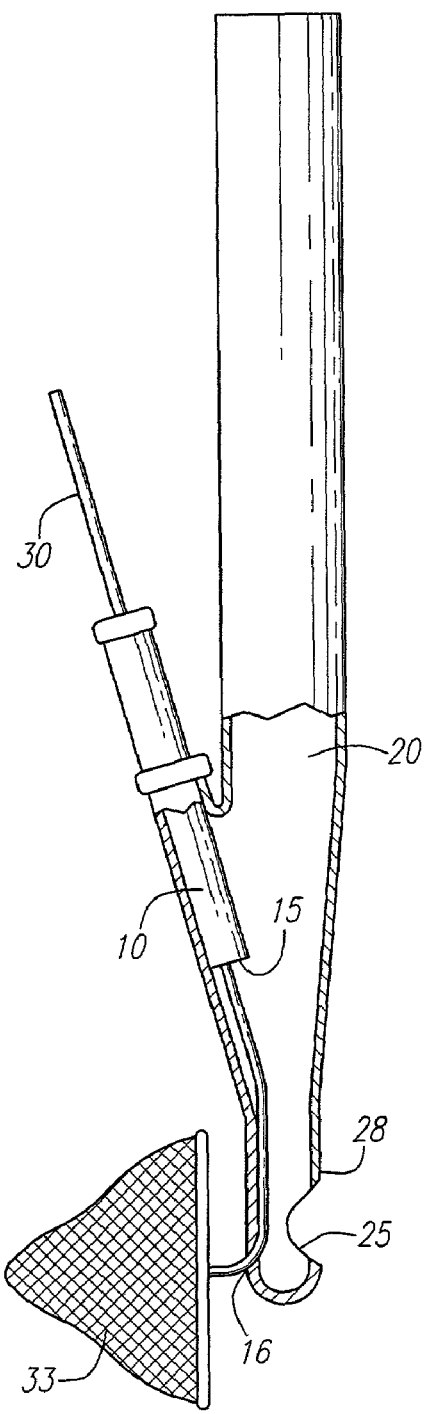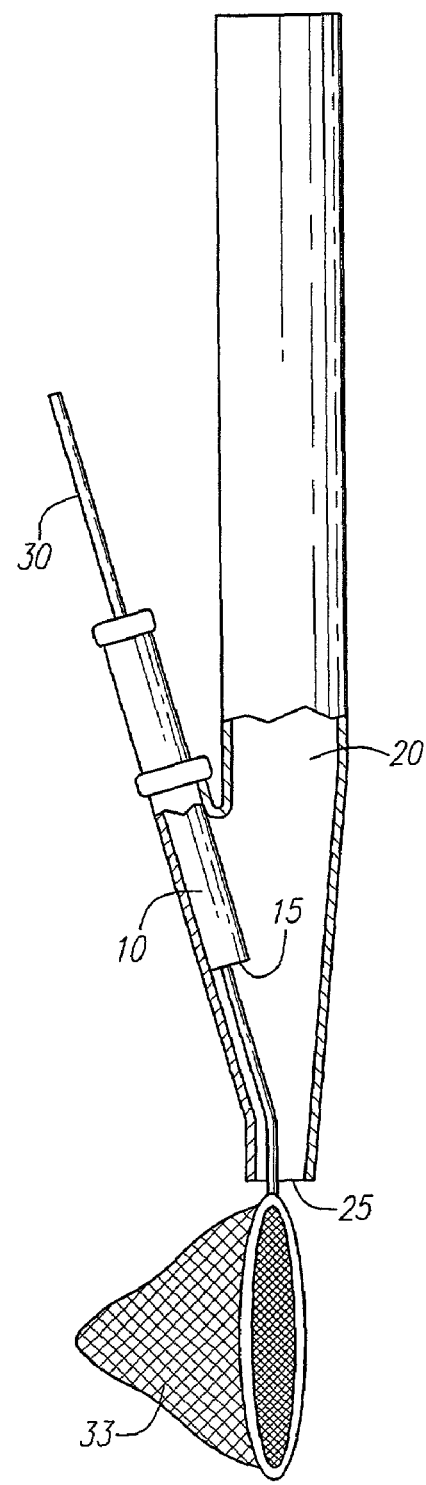
*FIG. 3A*   *FIG. 3B*

DIRECT ACCESS ATHERECTOMY DEVICES

This is a continuation-in-part of U.S. application Ser. No. 10/046,890, filed Jan. 14, 2002 now abandoned, which is incorporated herein by reference in its entirety.

FIELD OF THE INVENTION

The present invention relates to medical devices for excising mobile and non-mobile atheromatous plaque from cardiovascular tissues, such as the aorta, the aortic valve, and/or the atria. More particularly, the devices employ a blood filter and/or mesh on the atherectomy catheter for preventing distal embolization.

BACKGROUND OF THE INVENTION

Arteriosclerosis, generally known for thickening and hardening of the arterial wall, is responsible for the majority of deaths in the United States and most westernized countries. Atherosclerosis, one type of arteriosclerosis, is the cause for disorder of the larger arteries that underlies most coronary artery disease, aortic aneurysm, arterial disease of the lower extremities, and cerebrovascular disease. Atherosclerosis is characterized by an accumulation of lipid-filled smooth muscle cells, macrophages, and fibrous tissues, commonly known as atheroma or plaque, in focal areas of cardiovascular tissues, especially the aorta.

Numerous approaches for treating the diseased aorta have been proposed, including balloon angioplasty, laser angioplasty, and atherectomy. Removal of the atheroma is generally performed percutaneously through insertion of medical devices, e.g., a catheter and/or imaging probe, through a peripheral artery, such as the femoral artery. The devices are then advanced to the region of interest through the aorta.

Unfortunately, there are several disadvantages associated with these approaches. First, inserting and manipulating devices through the aorta may cause significant aortic trauma, resulting in aortic dissection, aortic wall hematoma, and/or embolization of calcium plaque from the aortic wall. Embolization of aortic plaque is a common cause of cerebral infarction or ischemia. Second, patients who have significant aortic atherosclerosis often have diseased peripheral arteries. Insertion of medical devices through the stenotic femoral arteries is often difficult and risky, because distal embolization and occlusion of the lower extremities can arise as a result of manipulating the diseased femoral artery. Thirdly, mechanical manipulation of the aorta during cardiothoracic surgeries, either in open thoracotomy or minimally invasive procedures, is a common cause for dislodgment of plaque, causing embolic stroke. Excision of high-risk atheromatous plaque from the aorta or cardiac tissues prior to cardiothoracic surgeries is therefore desired. The percutaneous approach requires an additional incision on a peripheral artery and therefore involves additional risk of vascular trauma and embolization.

New devices and methods are therefore needed that provide direct access to a patient's cardiovascular tissue for removal of atheromatous plaque(s) prior to or during cardiovascular surgeries, and that minimize the risk of peripheral embolization.

SUMMARY OF THE INVENTION

The methods and systems of the present invention provide means of introducing a combination of multiple devices or instruments into a patient's cardiovascular tissue, such as the aorta or an atrium, through a single incision site, thereby reducing the number of incisions on the vessel and minimizing space crowding during vascular surgeries. More particularly, atherectomy devices and a blood filter, devices formerly introduced through the femoral artery, are introduced directly into the aorta or are inserted into the cardiovascular tissue through a cannula system, thereby avoiding trauma to the peripheral artery and providing protection against distal embolization. The methods and systems can be used in conventional or minimally invasive surgeries to provide perfusion, drug delivery, fluid infusion, filtration, and atherectomy.

In a first embodiment, the systems comprise a cannula system having a first lumen that communicates with a proximal end and a port at its distal end, and a second lumen that communicates with a proximal end and a port at its distal end. The proximal ends of the lumens are adapted to receive medical devices. A blood filter is inserted through the first lumen to capture embolic debris. An atherectomy catheter is inserted through the second lumen of the cannula system. The distal region of the catheter includes an atherectomy assembly, which is operable to remove atheroma from cardiovascular tissues.

In another embodiment, the first lumen of the cannula system merges and communicates with the second lumen so that the two lumens communicate with the same port at the distal region of the cannula system. A suture flange may be included on a distal region of the cannula system. A hemostatic valve may also be included in the first and/or second lumens.

In still another embodiment, the cannula system comprises a third lumen communicating with a proximal end and a perfusion port at its distal end. The lumen is adapted for perfusion of arterial blood, i.e. for use as an arterial return cannula in cardiopulmonary bypass. The proximal end is adapted-for-attachment to a bypass-oxygenator machine. The distal end may be angled relative to the proximal end to facilitate blood flow into the aorta. The cannula system and filter assemblies for use with the present invention include those described in Martinez et al., U.S. application Ser. No. 09/365,650, filed Aug. 2, 1999, incorporated herein by reference in its entirety.

The atherectomy catheter comprises a sheath having a lumen that communicates with a proximal end and an opening at a distal end. In some embodiments, the sheath terminates distally in a sharpened edge, capable of cutting an atheromatous plaque. In other embodiments, the atherectomy assembly comprises an elongate member that extends through the lumen of the sheath. A loop that is operable to remove an atheroma is mounted on the distal end of the elongate member. The elongate member is slideably moveable within the lumen of the sheath so that the loop is captured within the lumen or advanced distally beyond the opening of the sheath. In certain embodiments, the loop includes a mesh disposed about a circumference of the loop to capture removed atheroma, thereby preventing embolization. The atherectomy assembly may also comprise a clipping instrument, laser, hydraulic instrument at the distal end of the catheter, or any of the cutting assemblies described in Barbut et al., U.S. Pat. No. 5,662,671, incorporated herein by reference in its entirety.

Although the present invention is most useful in removing atheroniatous plaque from the aorta, it should be understood that the cannula system described herein can also be used to remove plaque in the cardiac chambers, heart valves, or peripheral arteries, e.g., the femoral arteries. In a first method, the distal end of the cannula system is inserted through an incision on the aorta. For, example, to perform atherectomy on plaque in the ascending aorta, the cannula system is inserted upstream or proximal to the inominate artery. Sutures are then placed on the suture flange, when included, to secure the cannula onto the aorta. An atherectomy catheter is inserted through the cannula system into the aorta and advanced to the region of interest. A blood filter is optionally inserted through the cannula system into the aorta and expanded to substantially cover the lumen of the aorta downstream of the aortic atheroma. The atheroma is removed by operating the atherectomy assembly from the proximal end. Removed atheroma and debris generated during the procedure are captured by the mesh mounted on the atherectomy assembly and/or the blood filter.

In another method of using the cannula system to perform aortic atherectomy, the cannula system, which includes the third lumen for arterial perfusion, is inserted upstream the inominate artery and downstream the aortic atheroma. A blood filter is inserted and expanded to entrap emboli. After circulatory isolation of the coronary vessels from the peripheral vascular system is achieved, e.g., using a vascular clamp, dam, or balloon occluder, the proximal end of the cannula system is attached to a bypass-oxygenator machine to deliver oxygenated blood to the aorta. After cardiopulmonary bypass is established, the atherectomy catheter is inserted through the cannula system into the aorta. In this way, atherectomy is performed before or during surgical procedures, e.g., coronary artery bypass grafting surgery.

It will be understood that there are several advantages to using the systems and methods disclosed herein for performing atherectomy in cardiovascular tissues. For example, the systems (1) permit a combination of therapies to be employed through only one incision site, thereby minimizing trauma to the cardiovascular tissue, (2) provide for atherectomy without making an incision on a peripheral artery, (3) reduce the number of devices used concomitantly, such as the filter and arterial cannula, thereby minimizing crowding in the surgical field, (4) provide a mesh and/or filter to capture embolic debris, thereby minimizing the risk of stroke, (5) can be employed in a variety of cardiac or vascular surgeries, and (6) can be used in minimally invasive procedures.

BRIEF DESCRIPTION OF THE DRAWINGS

FIG. 3A depicts another embodiment of the cannula system having the first lumen communicating with the second lumen.

FIG. 3B depicts another embodiment of the cannula system having two lumens communicating with the same distal port.

DETAILED DESCRIPTION

Figure 1A:
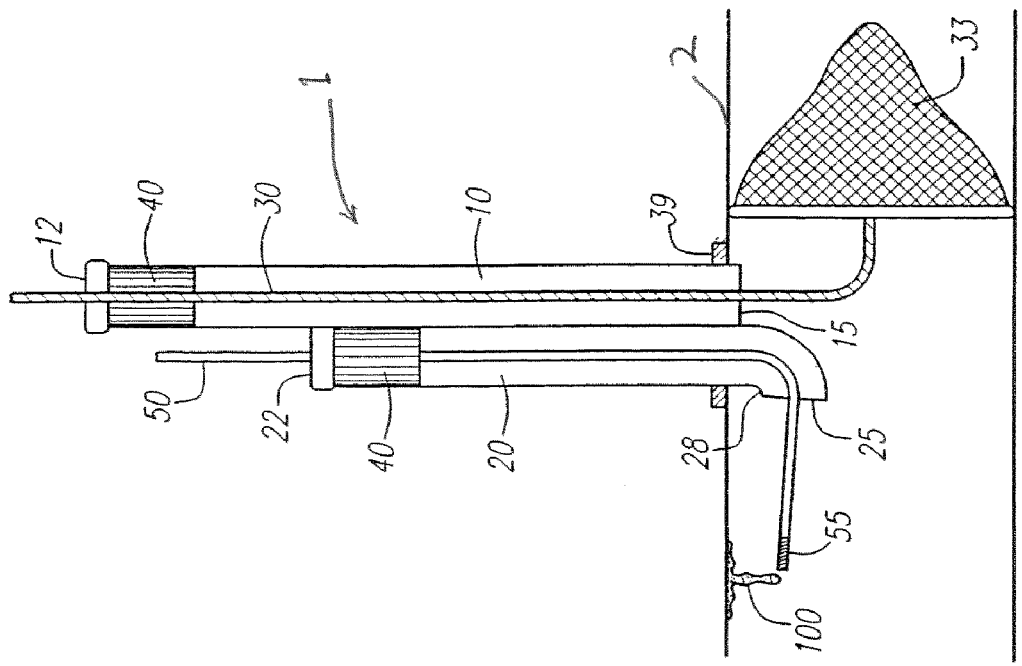
FIG. 1A depicts a cannula system for performing atherectomy on cardiovascular tissue according to the present invention.

The cannula systems described herein are useful for performing atherectomy inside a patient's vessel, e.g., the ascending aorta, the aortic arch, the descending aorta, the femoral artery, the iliac artery, the popliteal artery and cardiac tissues, e.g., the atrium, the aortic valves, and the mitral valves. FIG. 1A depicts an embodiment of a cannula system 1 having first lumen 10 communicating with proximal end 12 positionable outside a blood vessel 2, and port 15 at distal end 18 positionable inside the blood vessel 2, and second lumen 20 communicating with proximal end 22 positionable outside the blood vessel 2, and distal port 25 at distal end 28 positionable inside the blood vessel 2. Filter device 30 includes expandable filter 33 mounted at its distal end, and is inserted through lumen 10 to the interior of the blood vessel. Atherectomy catheter 50, which includes atherectomy assembly 55, is inserted through the second lumen 20 and port 25 to reach atheroma 100 inside the blood vessel 2. In certain embodiments, the distal region of the atherectomy catheter includes bendable region 51. Bendable region 51 assumes a linear configuration relative to its proximal end when housed within the second lumen 20 of the cannula system, and assumes a preformed angled configuration relative to its proximal end when protruding distally through the distal port 25 to facilitate positioning of assembly 55 close to the atheroma.

Figure 1B:
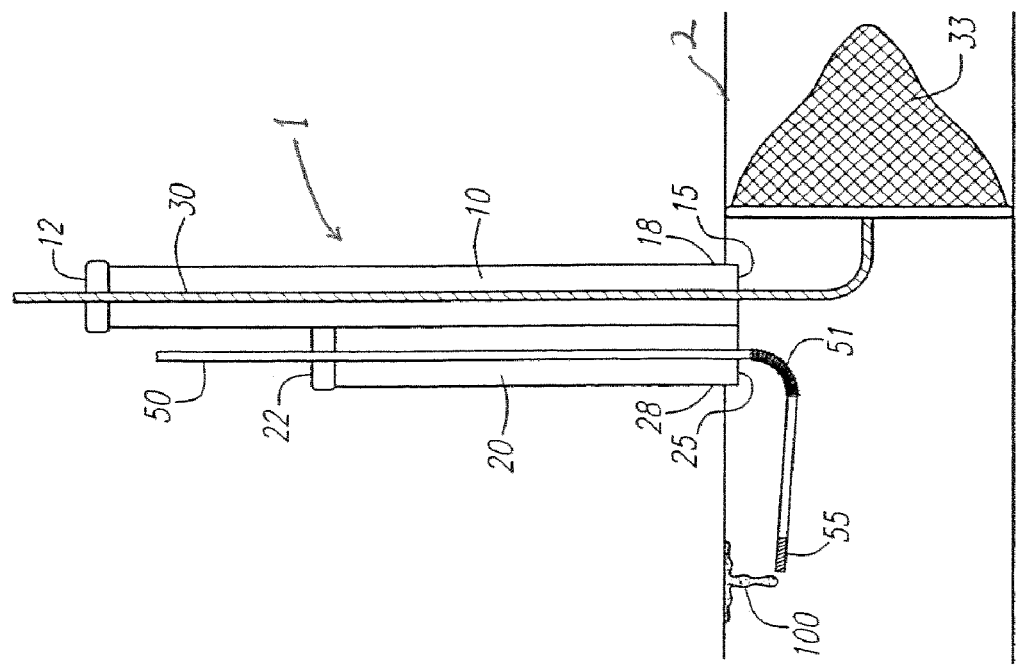
FIG. 1B depicts another embodiment of the cannula system having an angled distal end.

FIG. 1B depicts another embodiment of the cannula system which includes suture flange 39 for placement of sutures onto cardiovascular tissues. Distal end 28 of lumen 20 is angled relative to its proximal end 22. This configuration facilitates contact between atherectomy assembly 55 and atheroma 100 after catheter 50 passes through port 25. Lumens 10 and 20 also include hemostatic valves 40 to prevent blood loss through proximal ends 12 and 22.

By way of example, when the filter system as disclosed herein is intended for use in the aorta, the construction and use of expansion means and associated filter mesh have been thoroughly discussed in earlier applications including Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, filed Apr. 30, 1996, and Barbut et al., and U.S. application Ser. No. 08/645,762, filed May 14, 1996, all of which are incorporated herein by reference in their entirety.

Figure 2A:
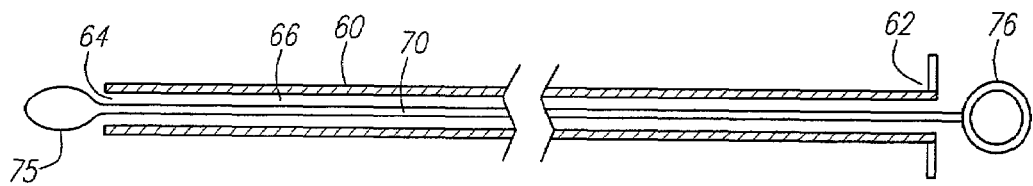
FIG. 2A depicts an atherectomy catheter having a loop mechanism at its distal end.
Figure 2B:
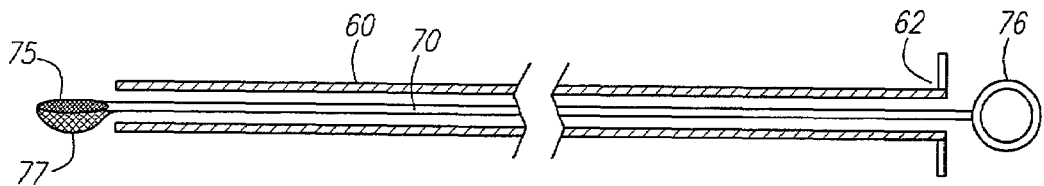
FIG. 2B depicts the atherectomy catheter of FIG. 2A having a mesh disposed about the loop.

FIGS. 2A through 2E depict different embodiments of the atherectomy assembly. In FIG. 2A, the atherectomy catheter comprises sheath 60 that has lumen 66 communicating with proximal end 62 and opening 64 at its distal end. Elongate member 70 passes through lumen 66 and includes loop 75 at its distal end. In use, loop 75 is retracted within lumen 66 during insertion of the catheter. After sheath 60 is positioned at the region of interest, loop 75 is extended distally beyond opening 64 of the sheath. Atheroma is then positioned within loop 75. Loop 75 is drawn proximally by pulling handle 76, thereby removing the atheroma. In certain embodiments, mesh 77 is disposed about a circumference of loop 75 as depicted in FIG. 2B to capture atheroma after removal, thereby preventing distal embolization.

Figure 2C:
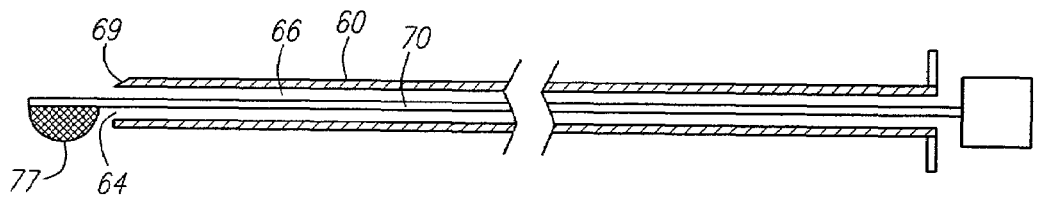
FIG. 2C depicts another embodiment of an atherectomy catheter, which includes a distal cutting sheath and mesh.

In FIG. 2C, the distal end of sheath 60 terminates in sharpened edge 69, which is adapted for cutting atheroma. Mesh 77 is disposed about the distal end of elongate member 70 for capturing atheroma after removal. In using the catheter, the distal end of elongate member 70 is housed within lumen 66 of the catheter during insertion of the catheter into the cardiovascular tissue. After the distal end of the catheter is positioned within the region of interest, mesh 77 is advanced distally and extends distal to opening 64. Atheroma is positioned within basket mesh 77, the elongate member is operated proximally to draw the atheroma against edge 69, the atheroma is excised using sharpened edge 69 and captured by mesh 77, thereby preventing distal embolization. Mesh 77 and the removed atheroma are then withdrawn into lumen 66 and removed from the patient together with sheath 66.

Figure 2D:
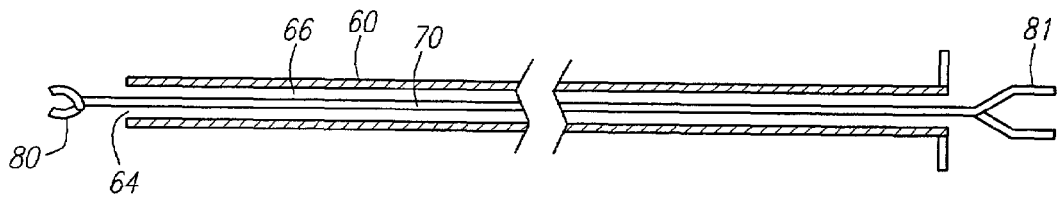
FIG. 2D depicts another embodiment of an atherectomy catheter having a pincer at its distal end.

FIG. 2D depicts another embodiment of the atherectomy assembly which comprises pincer 80 mounted at the distal end of elongate member 70. In use, pincer 80 is placed in a closed position and housed within lumen 66 during insertion of the catheter. After the catheter is advanced to the region of interest, elongate member 70 is advanced distally, extending pincer 80 distal to opening 64. Pincer 80 is opened by operating proximal handles 81 and is positioned at the base of the atheroma. Atheroma is separated and removed by closing the pincer.

Figure 2E:
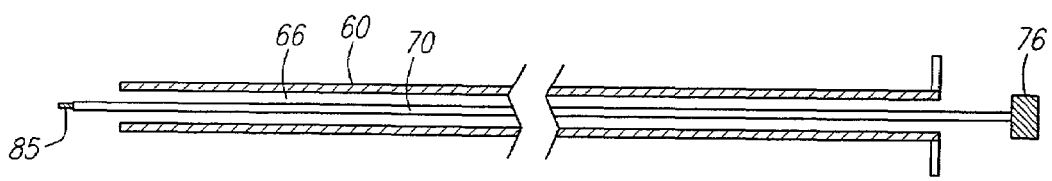
FIG. 2E depicts an atherectomy catheter having a laser probe mounted at its distal end.

FIG. 2E depicts another embodiment of the atherectomy assembly which comprises laser 85. In use, after the catheter is positioned within the region of interest, laser 85 is advanced distal to opening 64 of sheath 60 and is operable from proximal end 76 to remove atheroma.

Another embodiment of the cannula system useful for performing atherectomy is depicted in FIG. 3A. Opening 15 of the distal end of lumen 10 terminates within lumen 20, allowing communication between lumens 10 and 20. In an alternative embodiment, lumens 10 and 20 do not merge and communicate, but remain separate ports at the distal end of the cannula system. In use, filter device 30 is inserted through lumen 10 and extends distally through opening 16 in distal end 28 of lumen 20. An atherectomy catheter (not shown) is inserted in lumen 20 and advanced into the cardiovascular tissue through opening 25, which is located in distal end 28 at approximately 180 degree from opening 16. This design not only facilitates deployment of the filter device and atherectomy catheter in the vascular tissue, but also minimizes the incision on the vascular tissue because of its tapered distal end.

In FIG. 3B, lumen 10 communicates with lumen 20 through opening 15 at the distal end of lumen 10. In use, filter device 30 is inserted through lumen 10 and an atherectomy catheter (not shown) is inserted through lumen 20. Both the filter and atherectomy catheter are inserted into a patient's vascular tissue through opening 25.

Figure 4:
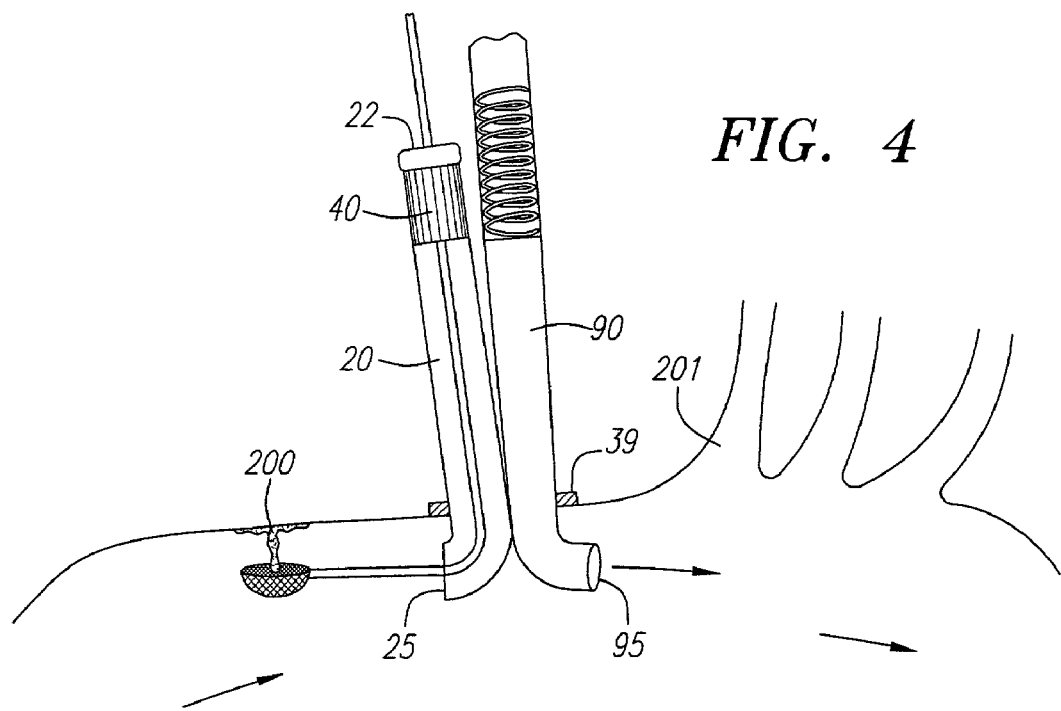
FIG. 4 depicts a cannula system inserted upstream the inominate artery for performing atherectomy and arterial perfusion in the ascending aorta.

FIG. 4 provides an embodiment of the cannula system that can be used to provide arterial perfusion and atherectomy. The cannula system comprises lumen 20 adapted for insertion of atherectomy catheter 50, and lumen 90 adapted for perfusion of oxygenated blood. In use, the cannula system is inserted in the ascending aorta upstream innominate artery 201. The distal end of the cannula system is secured onto the aorta by placing sutures between suture flange 39 and the aortic wall. The proximal end of lumen 90 is attached to a bypass-oxygenator machine. To establish cardiopulmonary bypass during cardiothoracic surgeries, for example, an aortic isolating device, such as an aortic clamp, balloon occluder is placed upstream atheroma 200, thereby isolating the coronary circulation from the peripheral vascular system. Simultaneously or shortly after delivery of cardioplegia solution to achieve cardiac arrest, oxygenated blood is delivered through lumen 90 and port 95 of the cannula system downstream in the aorta to perfuse the body organs. The atherectomy catheter of FIG. 2B is inserted into the ascending aorta to remove atheroma 200 through lumen 20 and port 25. Hemostatic valve 40 included in lumen 20 prevents blood loss through proximal end 22.

Alternatively, the atherectomy catheter is inserted into the aorta to perform atherectomy before the establishment of cardiopulmonary bypass. After the surgeon has performed the cardiovascular procedures, cardiopulmonary bypass is discontinued by removing aortic occlusion and stopping oxygenated blood infusion through lumen 90.

Figure 5:
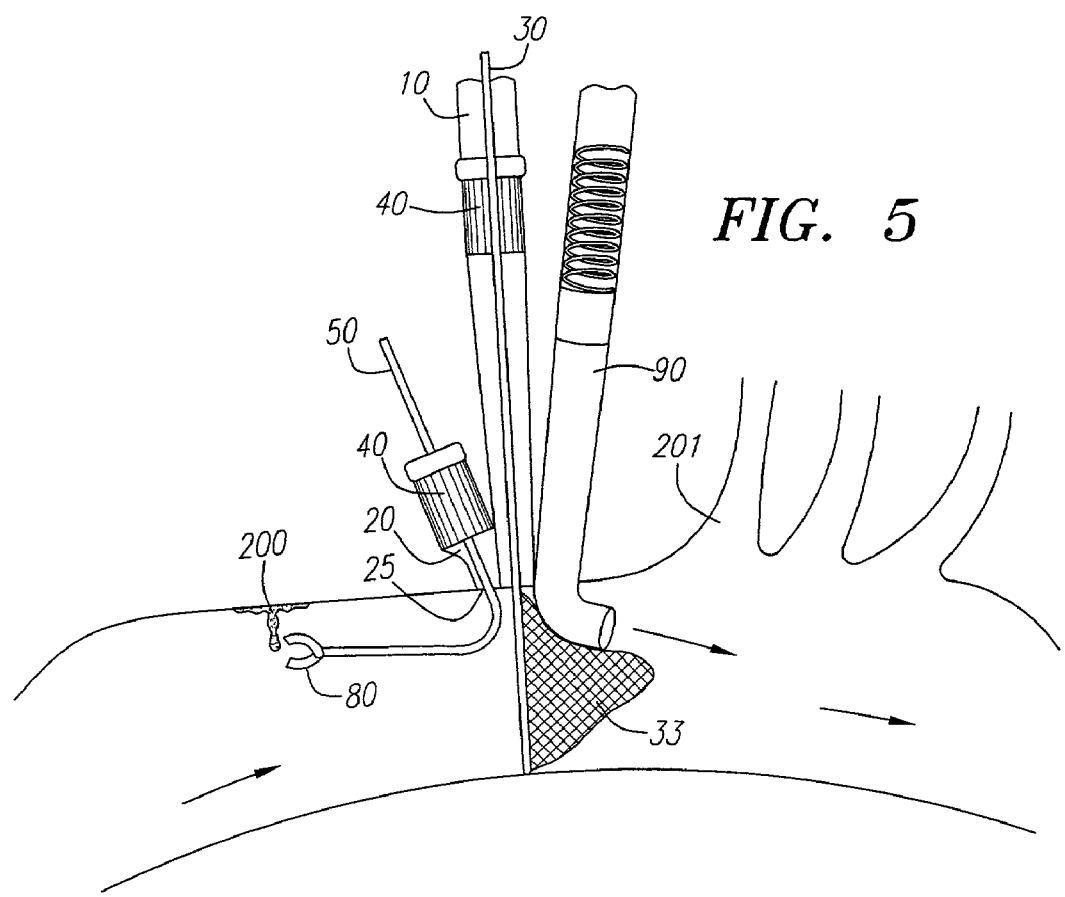
FIG. 5 depicts another embodiment of the cannula system of FIG. 4, which includes a blood filter.

FIG. 5 depicts another embodiment of the cannula system useful in performing atherectomy during cardiopulmonary bypass. The cannula system comprises lumen 90 for arterial perfusion, lumen 10 for insertion of blood filter 30, and lumen 20 for deployment of atherectomy catheter 50. In use, the cannula system is inserted in the ascending aorta upstream from the innominate artery 201. Cardiopulmonary bypass is established by attaching the proximal end of lumen 90 to a bypass-oxygenator machine. Filter device 30 is then inserted through lumen 10 and filter 33 is expanded to substantially cover the lumen of the aorta. The atherectomy catheter of FIG. 2D, or any other device shown in FIG. 2, is inserted through lumen 20 and port 25 to remove atheroma 200. Hemostatic valves 40 included in lumens 10 and 20 prevent blood loss. Embolic materials generated during atherectomy and cardiovascular procedures, including calcium, atheromatous plaque, myocardial tissue debris, and thrombi, are trapped by filter 33, thereby preventing distal embolization to the brain and peripheral organs causing tissue ischemia or death. The entrapped emboli are removed from the aorta by retracting device 30 proximally and compressing filter 33 within lumen 10.

The length of the cannula will generally be between 10 and 60 centimeters, more preferably approximately 20 to 35 centimeters, more preferably approximately 30 centimeters. The inner diameter of the lumen adapted for arterial perfusion will generally be between 0.5 and 1.5 centimeters, preferably approximately 1.0 centimeters. The length of the lumen adapted for insertion of filter device or atherectomy catheter will generally be between 2.0 and 10.0 centimeters, preferably approximately 6.0 centimeters. The inner diameter of this lumen will generally be between 0.2 and 1.2 centimeters, preferably approximately 0.6 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claims.

What is claimed is:

1. An atherectomy device for accessing the interior of a blood vessel from the exterior thereof and for removing an atheroma from the interior of a blood vessel, comprising:

a cannula system having a first lumen that extends from a proximal end outside of the blood vessel to a first distal port positionable in the interior of the blood vessel, and a second lumen that extends from a proximal end outside of the blood vessel to a second distal port positional in the interior of the blood vessel;

a filter insertable through the first lumen so as to extend through the first distal port into the interior of the blood vessel; and an atherectomy catheter insertable through the second lumen so as to extend through the second distal port into the interior of the blood vessel, the atherectomy catheter comprising:

a tubular sheath having an open distal end and a lumen extending from a proximal end to the open distal end; and an elongate member extending through the lumen of the sheath and having a distal end terminating in an atheroma removal element;

wherein the elongate member is movable axially in the lumen of the sheath between a first position in which the atheroma removal element is retracted within the lumen of the sheath, and a second position in which the atheroma removal element extends from the open distal end of the sheath, the atheroma removal element being operable to remove the atheroma by direct access to the interior of the blood vessel while the filter captures embolic debris in the interior of the blood vessel.

2. The atherectomy device of claim 1, wherein the atheroma removal element includes a loop.

3. The atherectomy device of claim 2, wherein the loop includes a mesh disposed about a circumference of the loop.

4. The atherectomy device of claim 1, wherein the atheroma removal element includes a pincer.

5. The atherectomy device of claim 1, wherein the atheroma removal element includes a laser.

6. The atherectomy device of claim 1, wherein the sheath terminates in distal cutting edge.

7. The atherectomy device of claim 1, further comprising a hemostatic valve in at least one of the first and second lumens of the cannula system.

* * * * *